United States Patent

Joshi et al.

(10) Patent No.: US 7,291,745 B2
(45) Date of Patent: Nov. 6, 2007

(54) PROCESS FOR THE PREPARATION OF PERINDOPRIL

(75) Inventors: Narendra Shriram Joshi, Koperkhairane (IN); Shekhar Bhaskar Bhirud, Vashi (IN); Kodali Eswara Rao, Koparkhairne (IN); Buddhavarapu Pattabhi Ramam, Koparkhairane (IN); Vijay Soni, Bridgewater, NJ (US)

(73) Assignee: Glenmark Pharmaceuticals Limited, Mumbai (IN)

( * ) Notice: Subject to any disclaimer, the term of this patent is extended or adjusted under 35 U.S.C. 154(b) by 0 days.

(21) Appl. No.: 11/386,011

(22) Filed: Mar. 21, 2006

(65) Prior Publication Data

US 2006/0211867 A1    Sep. 21, 2006

Related U.S. Application Data

(60) Provisional application No. 60/666,354, filed on Mar. 30, 2005.

(30) Foreign Application Priority Data

Mar. 21, 2005   (IN)   .................. 306/MUM/2005

(51) Int. Cl.
    *C07D 209/12*   (2006.01)
(52) U.S. Cl. .................................... 548/492
(58) Field of Classification Search ............. 548/492
    See application file for complete search history.

(56) References Cited

U.S. PATENT DOCUMENTS 4,914,214 A * 4/1990 Vincent et al. ............. 548/492

FOREIGN PATENT DOCUMENTS

| EP | 1 279 665 | 1/2003 |
|----|-----------|--------|
| EP | 1 367 061 | 12/2003 |
| ES | 2 004 804 | 2/1989 |
| WO | WO 96/33984 | 10/1996 |
| WO | WO 200158868 A1 * | 8/2001 |
| WO | WO 2004/075889 | 9/2004 |
| WO | WO 2005/105762 | 11/2005 |
| WO | WO 2005/113500 | 12/2005 |

OTHER PUBLICATIONS

Ogata Masaru et al., "N-(Chlorosulfinyl)-imidazole as a new imidazole transfer reagent" Synthetic Communications, 10(10), pp. 733-742 (1980).
Coll, Alberto Palomo, "Formation of new N-sulfoxyanhydrides as intermediates for the synthesis of ACE inhibitors" Afinidad 57(487), pp. 209-210(2000).

* cited by examiner

*Primary Examiner*—Joseph K. McKane
*Assistant Examiner*—Michael P. Barker
(74) *Attorney, Agent, or Firm*—M. Carmen & Associates, PLLC

(57) ABSTRACT

A process for preparing perindopril is provided comprising condensing an N-[(S)-1-carbethoxybutyl]-(S)-alanyl halide of formula II:

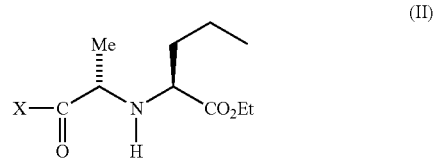

(II)

wherein X is a halide with an (2S,3aS,7aS)-2-carboxyperhydroindole of formula III:

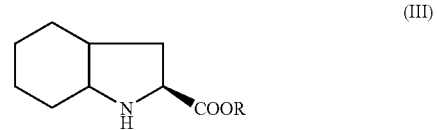

(III)

wherein R is hydrogen or a protecting group.

15 Claims, No Drawings

PROCESS FOR THE PREPARATION OF PERINDOPRIL

PRIORITY

This application claims the benefit under 35 U.S.C. §119 to U.S. Provisional Application No. 60/666,354, filed Mar. 30, 2005, and entitled PROCESS FOR THE PREPARATION OF PERINDOPRIL" and to Indian Provisional Application No. 306/MUM/2005, filed Mar. 21, 2005, and entitled "PROCESS FOR THE PREPARATION OF PERINDOPRIL AND SALTS THEREOF", the contents of each of which are incorporated by reference herein.

BACKGROUND OF THE INVENTION

1. Technical Field

The present invention generally relates to an improved process for the preparation of perindopril and pharmaceutically acceptable salts thereof. More specifically, the present invention relates to a process which forms a novel intermediate in the preparation of perindopril erbumine.

2. Description of the Related Art

Perindopril erbumine, also known as (2S,3aS,7aS)-1-[(S)-N-[(S)-1-carboxy-butyl]alanyl]hexahydro-2-indolinecarboxylic acid, 1-ethyl ester, compound with tert-butylamine (1:1), is represented by the structure of Formula I.

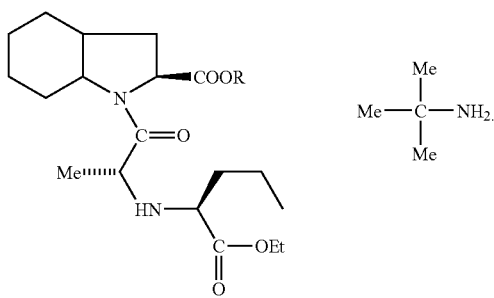

The tert-butylamine salt of perindopril, also known as perindopril erbumine, is the form commercially sold under the trade name Aceon®. Perindopril is the free acid form of perindopril erbumine and is an ethyl ester of a non-sulfhydryl angiotensin-converting enzyme (ACE) inhibitor. Perindopril is also a pro-drug and is metabolized in vivo by hydrolysis of the ester group to form perindoprilat, the biologically active metabolite. Perindopril is ordinarily used to treat hypertension.

It is believed that perindopril lowers blood pressure primarily through inhibition of ACE activity. ACE is a peptidyl dipeptidase that catalyzes conversion of the inactive decapeptide, angiotensin I, to the vasoconstrictor, angiotensin II. Angiotensin II is a potent peripheral vasoconstrictor, which stimulates aldosterone secretion by the adrenal cortex, and provides negative feedback on renin secretion. Inhibition of ACE results in decreased plasma angiotensin II, leading to decreased vasoconstriction, increased plasma renin activity and decreased aldosterone secretion. The latter results in diuresis and natriuresis and may be associated with a small increase in serum potassium.

U.S. Pat. No. 4,914,214 ("the '214 patent"), incorporated by reference herein, discloses a process for the preparation of perindopril. A process disclosed in the '214 patent for the preparation of perindopril involves hydrogenating indoline-2-carboxylic acid (1) in methanol over a rhodium-aluminum oxide ($Rh/Al_2O_3$) catalyst to form (2S,3aS,7aS)-octahydroindole-2-carboxylic acid of the formula (2). The acid of formula (2) is then esterified with thionyl chloride and benzyl alcohol to yield (2S,3aS,7aS)-octahydroindole-2-carboxylic acid benzyl ester (3), which is one key intermediate of perindopril. Another key intermediate of perindopril is prepared by reacting L-norvaline (4) with thionyl chloride and ethanol to form an ethyl ester (5). The ethyl ester (5) is reacted with sodium pyruvate (6) and subjected to hydrogenation to form N-1S-carboxyethylbutyl-(S)-alanine (7), another key intermediate. (2S,3aS,7aS)-octahydroindole-2-carboxylic acid benzyl ester (3) is then coupled with N-1S-carboxyethylbutyl-(S)-alanine (7) in presence of sodium dicyclohexyl dicarbodiimide (DCC) to yield perindopril benzylated ester (8). Perindopril benzylated ester (8) is hydrolyzed to form perindopril (9). Perindopril (9) is reacted with tert-butylamine to form the perindopril erbumine salt (I) as generally shown below in Scheme I.

SCHEME I

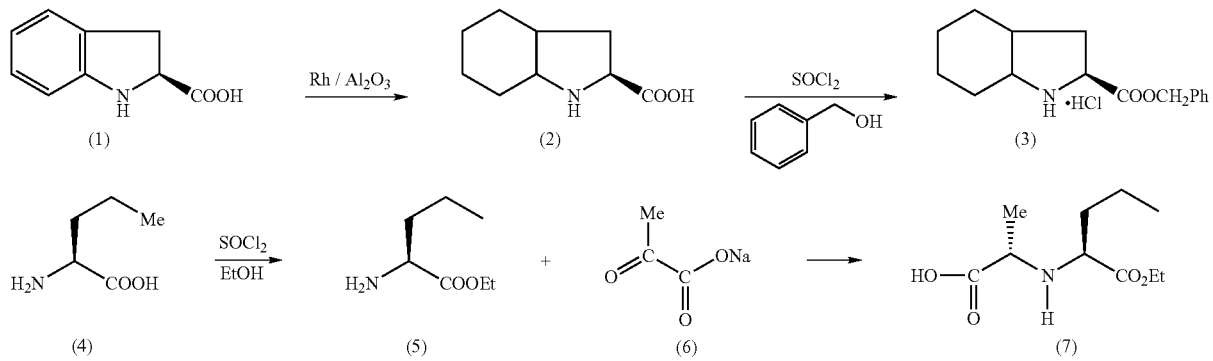

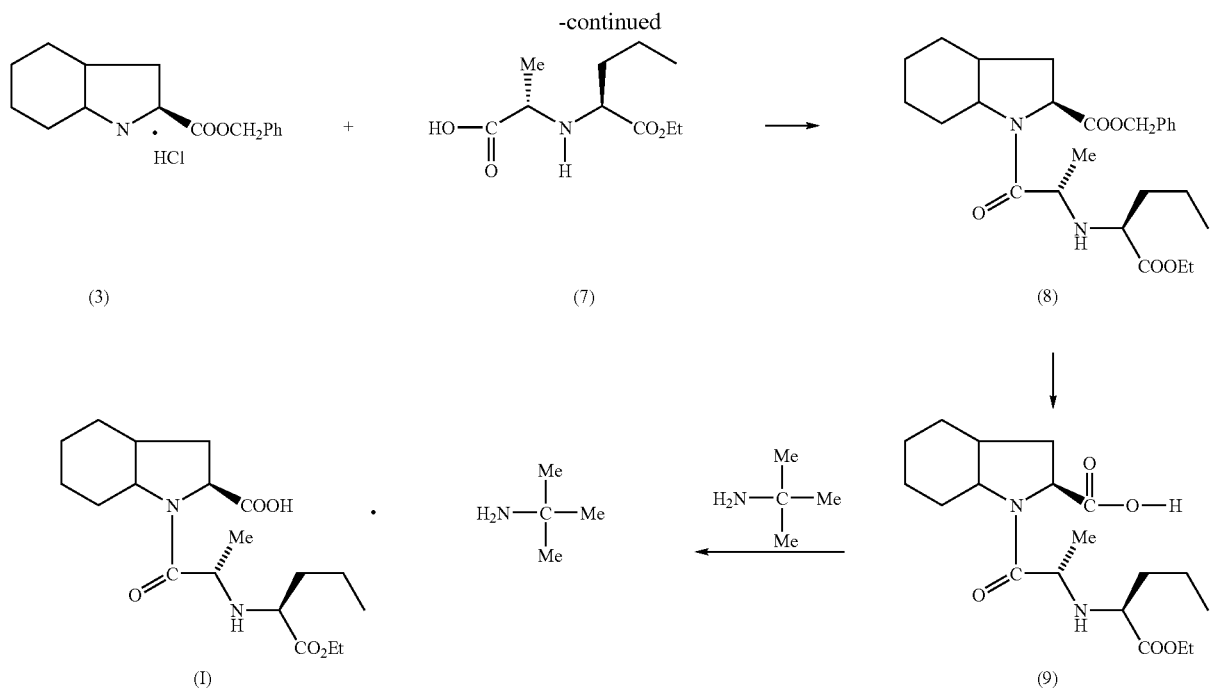

WO 2004/075889, incorporated by reference herein, also discloses a process for preparing perindopril which includes reacting the benzyl ester of (2S, 3aS, 7aS)-2-carboxyperhydroindole with N-[(S)-1-carbethoxybutyl]-(S)-alanyl chloride or bromide in the presence of a suitable base followed by debenzylation by catalytic hydrogenation. However, this method is relatively time consuming and not cost effective because the debenzylation uses a Pd/C catalyst.

Several drawbacks are further associated with the processes of the prior art. For example, several drawbacks include the use of toxic reagents with stringent standards, expensive reagents that are not easily recycled, and numerous steps that add to process inefficiencies and complications during commercial production.

Accordingly, there remains a need for improved processes for preparing perindopril that eliminate and reduce the drawbacks of the prior art in a convenient and cost efficient manner on a commercial scale.

SUMMARY OF THE INVENTION

In accordance with one embodiment of the present invention, a process for the preparation of perindopril and pharmaceutically acceptable salts thereof are provided, the process comprising condensing of an N-[(S)-1-carbethoxybutyl]-(S)-alanyl halide of formula II:

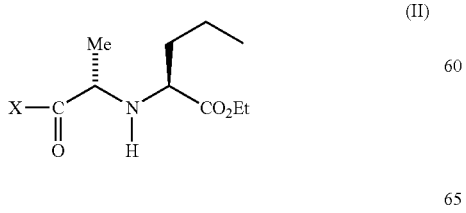

(II)

wherein X is a halide with an (2S,3aS,7aS)-2-carboxyperhydroindole of formula III:

(III)

wherein R is hydrogen or a protecting group.

DETAILED DESCRIPTION OF THE PREFERRED EMBODIMENTS

In one aspect of the present invention, a process for preparing perindopril is provided which includes at least condensing an N-[(S)-1-carbethoxybutyl]-(S)-alanyl halide of formula II with an (2S,3aS,7aS)-2-carboxyperhydroindole of formula III as generally shown in Scheme II:

SCHEME II

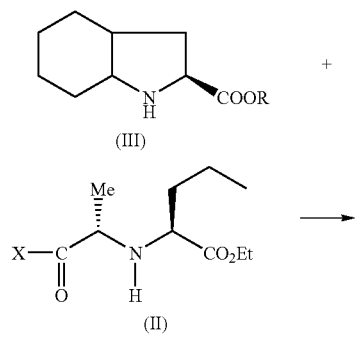

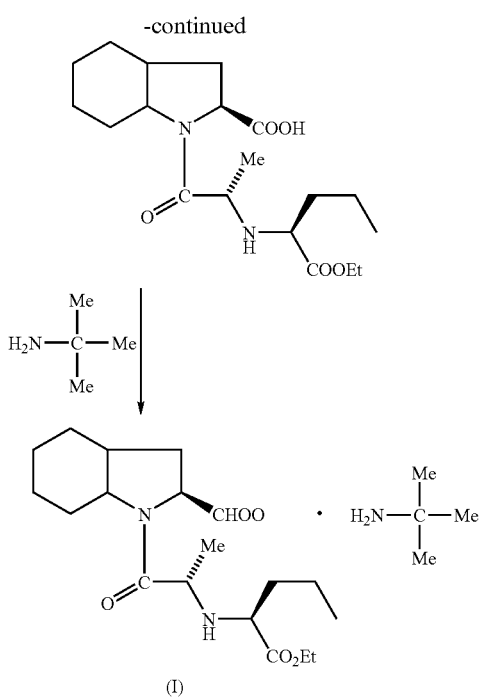

wherein R may be hydrogen or a protecting group, and X is a halide, e.g., bromide, chloride, etc. Useful protecting groups include those represented by the formula $Si(R^1)(R^2)(R^3)$, wherein $R^1$, $R^2$ and $R^3$ are independently a straight or branched alkyl or aryl group having from 1 to about 25 carbon atoms. The reaction can be carried out in an organic solvent at low to ambient temperature and in the presence of a base to facilitate formation of perindopril. The (2S, 3aS, 7aS)-2-carboxyperhydroindole of formula III may be present in a molar ratio of about 0.9:1 to about 1:1 moles per moles of the compound of formula II.

The reaction of a compound of formula II with a compound of formula III may be conducted in one or more organic solvents such as, for example, one or more anhydrous solvents. Suitable anhydrous solvents include, but are not limited to halogenated hydrocarbons, e.g., dichloromethane, dichloroethane, and the like; aromatic hydrocarbons, e.g., benzene, toluene, and the like; aliphatic hydrocarbons, e.g., hexane, heptanes, and the like; cycloaliphatic hydrocarbons, e.g., cyclopentane, cyclohexane, and the like; and mixtures thereof. Preferably, the solvent used is one or more chlorinated hydrocarbons.

The reaction can also be carried out in the presence of one or more organic bases such as, for example, imidazole, triethylamine, diethylamine, pyridine, n-methyl morpholine and the like, with imidazole being preferred. Typically, the base is employed in molar proportions of about 2 to about 5 moles per mole of a compound of formula II, and preferably about 2 to about 4 moles per mole of a compound of formula II.

The reaction may be carried out at low to ambient temperatures ranging from about −20° C. to about 30° C., and preferably from about 5° C. to about 10° C. The reaction time may range from about 1 hour to about 12 hours depending on the temperature employed.

Perindopril erbumine may be formed in situ by treatment with tert-butylamine. After completion of the reaction, the pH may be adjusted to a level of about 4 to about 5 by addition of a suitable mineral acid, e.g., a hydrochloric acid medium. The organic layer may be separated, washed with water, dried and/or further reacted with tert-butylamine. After evaporation of the solvent, perindopril erbumine is obtained from conventional crystallization techniques.

The N-[(S)-1-carbethoxybutyl]-(S)-alanyl halide may be formed by reacting N-[(S)-1-carbethoxybutyl]-(S)-alanine with a halogenating agent in a suitable anhydrous solvent and in the presence or absence of an inert gas. Suitable anhydrous solvents include any of those discussed hereinabove. Preferably, the solvent employed is one or more chlorinated hydrocarbons. Suitable inert gases include, but are not limited to, nitrogen, argon etc.

The (2S, 3aS, 7aS)-2-carboxyperhydroindole may be reacted with a compound of formula II with the carboxy group protected or not protected. The protection group may be, for example, a silyl protecting group. This can be accomplished by converting the carboxylic acid to the silyl ester by reaction with a trialkyl or aryl silyl chloride in the presence of an organic base. The silyl protected (2S, 3aS, 7aS)-2-carboxyperhydroindole may then be reacted in situ with the N-[(S)-1-carbethoxybutyl]-(S)-alanyl halide.

In the case where a protecting group is used, after completion of the reaction, desillyation can be carried out by adjusting the pH to about 4 to about 5 by addition of a suitable mineral acid. The organic layer is separated and after washing with water, dried and in situ reacted with tert-butyl amine to provide perindopril erbumine.

The following examples are provided to enable one skilled in the art to practice the invention and are merely illustrative of the invention. The examples should not be read as limiting the scope of the invention as defined in the claims.

EXAMPLE 1

Preparation of N-[1-(S)-ethoxycarbonyl-1-butyl]-(S)-alanyl Chloride Hydrochloride Into a 4-neck round bottom flask, methylene chloride (700 ml) and phosphorous pentachloride (148 gm) were added and stirred for 90 minutes at a temperature ranging from about 20° C. to about 25° C. and then cooled to a temperature of about −10° C. Next, N-1(S)-carboxyethylbutyl-(S)-alanine (100 gm) was added and the temperature was maintained for 5 hours at a temperature ranging from about −5° C. to about 0° C. Diisopropyl ether (2.0 L) was slowly added while the temperature was kept below −5° C. and then maintained at a temperature ranging from about −5° C. to about 0° C. for about 1 hour. The solid was filtered under a nitrogen atmosphere and the filtered material was dried at a temperature ranging from about 40° C. to about 45° C. under vacuum. Dry wt. 122 gms.

EXAMPLE 2

Preparation of Perindopril Erbumine

Into a 4-neck round bottom flask, methylene chloride (2000 ml) and N-1(S)-carboxyethylbutyl-(S)-alanyl chloride hydrochloride (177 g) were added and cooled to a temperature of about −5° C. To this mixture was added imidazole (161 g) and the temperature was maintained for about 1 hour at a temperature below about 0° C. Next, (2S, 3aS, 7aS)-2-carboxyperhydroindole (100 g) was added slowly in about 45 minutes. The reaction mass was then stirred for about 2 hours at a temperature of about −5 to 0° C. The temperature was raised to a temperature ranging from about 20° C. to about 25° C. and maintained for 2 hours. A mixture of acetic acid (106 g) in water (1 L) was added while the temperature was kept below 5° C. and stirred for 30 minutes. The methylene chloride layer was separated and then washed with saturated brine solution (200 ml) and dried over sodium sulfate (10 g). The methylene chloride layer was charged in a round bottom flask and cooled to a temperature of about 10° C.

Next, tert-butyl amine (65 ml) was charged in 30 minutes at a temperature below 10° C. and stirred further for 30 minutes at 35-40° C. The methylene chloride was then distilled off completely. A mixture of isopropyl alcohol (300 ml), acetone (600 ml) and acetonitrile (600 ml) was charged and added to the separated methylene chloride. The mixture was heated to a temperature ranging from about 65° C. to about 70° C. to get a clear solution. The reaction mass was cooled very slowly to a temperature of about 25° C. in 2 hours and then further cooled to a temperature ranging from about 5° C. to about 10° C. and filtered. The filtered material was then dried under vacuum at a temperature of about 40° C. (Weight: 124 gm, purity: >99.5% by HPLC).

Specific optical rotation $[\alpha]n=-66$ (C=1%, Methanol), IR (KBr) spectrum shows the following absorptions $cm^{-1}$ 3300, 2930, 1744, 1732 m 1644 m 1568. The $^1$H-NMR (CDCl$_3$) shows the following signals at δ 4.28-4.12 (m, 1H), 4.18-4.09 (q,2H), 3.76 (m,2H) 3.53 (q, 1H), 3.1 (t, 1H), 2.32-2.14 (m, 2H), 2.01 (m, 1H), 1.75-1.62 (m, 4H), 1.32 (m, 2H), 1.30 (S, 9H), 1.28 (t, 3H), 0.88 (t, 3H). C.I. Mass shows m/z at 368 (base peak.) XRD matches with α-polymorph.

EXAMPLE 3

Preparation of Perindopril Erbumine

Step A

Into a 4-neck round bottom flask, methylene chloride (50 ml) and (2S, 3aS, 7aS)-2-carboxyperhydroindole (5 g) were added and cooled to a temperature of about 10° C. Next, trimethyl silyl chloride (3.21 g) was added dropwise at a temperature below 10° C. While stirring for 10 minutes, imidazole (2 g) was added at a temperature below 10° C. The reaction mass was then stirred for about 2 hours at a temperature ranging from about 10° C. to about 15° C. to yield a trimethyl silyl ester of (2S, 3aS, 7aS)-2-carboxyperhydroindole.

Step B

Into another 4-neck round bottom flask methylene chloride (100 ml) and N-1(S)-carboxyethylbutyl-(S)-alanyl chloride (8.85 g) were added and cooled to a temperature of about 10° C. Imidazole (8.04 gm) was added at a temperature below 10° C. and maintained for 1 hour at a temperature ranging from about 10° C. to about 15° C.

Step C

The trimethyl silyl ester of (2S, 3aS, 7aS)-2-carboxyperhydroindole of Step A was added dropwise to the compound of Step B in 1 hour at a temperature of about 10° C. The reaction mixture was stirred for about 2 hours at a temperature of about 10° C. A mixture of acetic acid (5.32 g) in methylene chloride (20 ml) was added while the temperature was kept below 5° C. and stirred for 30 minutes. Water (30 ml) was added and stirred for about 30 minutes. The methylene chloride layer was separated and then washed with saturated brine solution (15 ml) and dried over sodium sulfate. The methylene chloride layer was charged in a round bottom flask and cooled to a temperature of about 5° C.

Next, tert-butylamine (3.25 ml) was charged in 30 minutes at a temperature below 10° C. and stirred further for 30 minutes at a temperature ranging from about 35° C. to about 40° C. Methylene chloride was then distilled off completely. A mixture of isopropyl alcohol (15 ml), acetone (30 ml) and acetonitrile (30 ml) was charged and added to the separated methylene chloride. The mixture was heated to a temperature ranging from about 65° C. to about 70° C. to get a clear solution. The reaction mass was cooled very slowly to a temperature of about 25° C. in 2 hours and then further cooled to a temperature ranging from about 5° C. to about 10° C. and filtered. The filtered material was then dried under vacuum at a temperature of about 40° C. (Weight: 7.0 g, purity: >99.5% by HPLC). Specific optical rotation $[\alpha]n=-66$ (C=1%, MeOH), IR (KBr) spectrum shows the following absorptions $cm^{-1}$ 3300, 2930, 1744, 1732 m 1644 m 1568. The $^1$H-NMR (CDCl$_3$) shows the following signals at δ 4.28-4.12 (m, 1H), 4.18-4.09 (q,2H), 3.76 (m,2H) 3.53 (q, 1H), 3.1 (t, 1H), 2.32-2.14 (m, 2H), 2.01 (m, 1H), 1.75-1.62 (m, 4H), 1.32 (m, 2H), 1.30 (S, 9H), 1.28 (t, 3H), 0.88 (t, 3H). CI Mass shows m/z at 368 (base peak.) XRD matches with α-polymorph.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A process for the preparation of perindopril comprising condensing an N-[(S)-1-carbethoxybutyl]-(S)-alanyl halide of formula II:

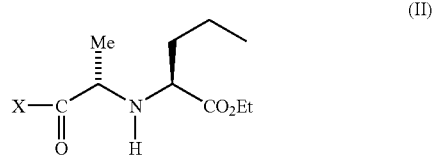

wherein X is a halide with an (2S,3aS,7aS)-2-carboxyperhydroindole of formula III:

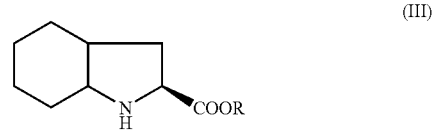

wherein R is $Si(R^1)(R^2)(R^3)$, and wherein $R^1$, $R^2$ and $R^3$ are independently a straight or branched alkyl or aryl group having from 1 to about 25 carbon atoms.

2. The process of claim 1, wherein the step of condensing is carried out in one or more organic solvents and in the presence of a base.

3. The process of claim 2, wherein the organic solvent is one or more anhydrous solvents.

4. The process of claim 3, wherein the one or more anhydrous solvents are selected from the group consisting of a chlorinated hydrocarbon, aromatic hydrocarbon, aliphatic hydrocarbon, cycloaliphatic hydrocarbon and mixtures thereof.

5. The process of claim 4, wherein the chlorinated hydrocarbon is selected from the group consisting of dichloromethane, dichloroethane and mixtures thereof.

6. The process of claim 4, wherein the aromatic hydrocarbon is selected from the group consisting of benzene, toluene, and mixtures thereof.

7. The process of claim 4, wherein the aliphatic hydrocarbon is selected from the group consisting of hexane, heptane, and mixtures thereof.

8. The process of claim 4, wherein the cycloaliphatic hydrocarbon is selected from the group consisting of cyclopentane, cyclohexane and mixtures thereof.

9. The process of claim 2, wherein the base is an organic base selected from the group consisting of imidazole, triethylamine, diethylamine, pyridine, n-methyl, morpholine and mixtures thereof.

10. The process of claim 2, wherein the base is present in a molar proportion of about 2 to about 5 moles per mole of the N-[(S)-1-carbethoxybutyl]-(S)-alanyl halide of formula III.

11. The process of claim 1, wherein the N-[(S)-1-carbethoxybutyl]-(S)-alanyl halide of formula II is formed by reacting N-[(S)-1-carbethoxybutyl]-(S)-alanine with a halogenating agent in a suitable anhydrous solvent and in the presence or absence of an inert gas.

12. The process of claim 1, wherein perindopril is thereafter converted to perindopril erbumine.

13. The process of claim 1, further comprising treating perindopril with tert-butylamine to provide perindopril erbumine.

14. The process of claim 1, further comprising adjusting the pH to about 4 to about 5 and subsequently reacting with tert-butylamine.

15. The process of claim 1, further comprising purifying perindopril erbumine.

* * * * *